United States Patent [19]
Duroselle

[11] Patent Number: 6,096,266
[45] Date of Patent: Aug. 1, 2000

[54] METHOD FOR DISINFECTING AND STERILIZING MICROBIAL CONTAMINATED MATERIALS

[75] Inventor: Patrick Duroselle, Saint-Herblain, France

[73] Assignee: Box 03 International, Gumligen, Switzerland

[21] Appl. No.: 09/113,699

[22] Filed: Jul. 10, 1998

[51] Int. Cl.[7] ...................................................... A61L 9/00
[52] U.S. Cl. ................................ 422/33; 422/28; 422/29; 422/32
[58] Field of Search .................................. 422/1, 28, 29, 422/32, 33

[56] References Cited

U.S. PATENT DOCUMENTS

| | | | |
|---|---|---|---|
| 4,680,163 | 7/1987 | Blidschun et al. | 422/28 |
| 5,077,008 | 12/1991 | Kralovic et al. | 422/37 |
| 5,374,394 | 12/1994 | Kralovic | 422/28 |

FOREIGN PATENT DOCUMENTS

| | | | |
|---|---|---|---|
| 7-136236 | 5/1995 | Japan | A61L 2/20 |

*Primary Examiner*—Krisanne Thornton
*Attorney, Agent, or Firm*—Limbach & Limbach L.L.P.

[57] ABSTRACT

Microbial contaminated materials, such as medical instruments and waste from medical laboratories or hospitals, are disinfected and sterilized by using a combination of peracetic acid and ozone in a sterilization chamber. The peracetic acid is formed within the sterilization chamber by introducing liquid hydrogen peroxide and liquid acetic acid into the chamber.

17 Claims, No Drawings

METHOD FOR DISINFECTING AND STERILIZING MICROBIAL CONTAMINATED MATERIALS

The present invention relates to a method for disinfecting and sterilizing microbial contaminated materials, e.g. medical devices, instruments, waste from laboratories or hospitals comprising blood or blood components or other biological material under use of a combination of in situ generated peracetic acid and ozone.

For disinfecting of medical devices, working tools or infectious waste material in the medical field, several methods using ozone are suggested according to prior art. The main problem of known methods has been the long period for treating the material containing pathogenic agents such as bacteria and viruses with a shorter treatment problems occurred with material containing biological liquids such as blood or components thereof (probably due to hemoglobin presence) because an amount of resistant spores survived. It was found that an improvement can be attained if a combination of ozone and peracetic acid was used in a humidified gaseous phase. Up to now peracetic acid has been used in liquid form for decontaminating medical wastes (U.S. Pat. No. 5,374,394) and the combination of peracetic add and ozone as a disinfectant has never been used in liquid form. Another approach is described in the document JP-7-136236 wherein hot vapor is injected into a sterilization chamber. The use of a hot oxidizing agent can be irritating and dangerous in the case of a defect in the chamber.

The present invention is related to a method for disinfecting and sterilizing microbial contaminated or infectious materials, e.g. medical instruments, waste from medical laboratories or hospitals. The method comprises the steps:

(a) loading the material for disinfecting and sterilizing into a pressure-proof sterilization chamber (b) introducing liquid hydrogen peroxide into the sterilization chamber so as to penetrate the material;

(c) introducing liquid acetic acid into the sterilization chamber so as to penetrate the material;

(d) evacuating gas from the sterilization chamber so as to evaporate the liquid at least partially;

(e) introducing gaseous ozone into the sterilization chamber;

(f) treating the material in the sterilization chamber for a sufficient time period so as to disinfect and sterilize the materials.

The method can be carried out in treatment devices as described in the patent documents EP-A-0 664 715 and EP-A-0 761 237, which can be adapted to the method according to present invention.

The method of the present invention is carried out, as a rule, at a temperature of about 15° C. to 35° C. and preferably at ambient temperature.

The hydrogen peroxide and the acetic acid can be introduced enclosed in two separate ampoules having such properties that after the evacuation of the chamber they are burst with release of the hydrogen peroxide and the acetic acid.

Alternatively the hydrogen peroxide and the acetic acid can be introduced enclosed in a container having at least two compartments being constructed in such a manner that the two compartments release their contents during the evacuation of the sterilizing chamber.

The method of the invention can be carried out in two or more cycles by feeding at least two times hydrogen peroxide, the acetic acid and/or ozone into the sterilization chamber.

Alternatively the sterilization chamber can be equipped with storage and feeding means for feeding continuously hydrogen peroxide, acetic acid and ozone in several process cycles.

The molar ratio of acetic acid to ozone according to the invention is as a rule about 3/1 to 1/3 and the humidity in the chamber is at least 10%.

The infectious waste material treated according to the method of the present invention can be solid material or a mixture of solid and liquid material. For disinfecting waste material safely, it is ground or broken up in other wise before, during or after the treatment with the disinfecting agents (hydrogen peroxide and acetic acid).

Preferably a stable, storable and shippable disinfecting and sterilizing combination of agents is used together with ozone in the method of the invention. The combination possesses improved properties and comprises a two-part system: the first part consists of a mixture of acetic acid and water, and the second consists of hydrogen peroxide and water. In this solution the peracetic acid is formed in situ. With this measure it is possible to take advantage of the outstanding disinfecting and sterilizing properties of peracetic acid without exposure to the danger of explosion and to the strong irritating properties to the skin and the eyes. The application of the peracetic acid forming combination with ozone Is carried out in a gaseous phase under reduced pressure (pressure<atmospheric pressure) and at ambient temperature. Hydrogen peroxide reacts with acetic acid to form of peracetic acid and water:

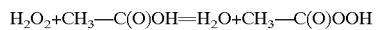

$$H_2O_2 + CH_3\text{---}C(O)OH = H_2O + CH_3\text{---}C(O)OOH$$

This is an equilibrium which can be shifted if the reaction takes place in the presence of a catalytic amount of acid (e.g. sulfuric acid). After termination of the disinfecting process the remaining ozone is destroyed, and, if necessary, the acid can be neutralized.

The present invention is illustrated with sterilizing tests carried out in a sterilizing apparatus of the type "BOX 03" of Carbagas Aktiengesellschaft CH 3097 Liebefeld (Switzerland). This apparatus was designed for disinfecting infectious waste material. Normally in this device the waste material is ground, gevacuated and treated one or several times with gaseous ozone In a sterilizing chamber. According to the present invention in situ-formed peracetic add is used additionally. For comparison, instead of peracetic acid only hydrogen peroxide was used. For the test, pads loaded with infected sheep's blood were used. The results are listed in the table below.

TABLE

Number of viable and sporular bacterial forms destroyed in a sterilization chamber on a pad in the presence of blood of a sheep (100 μl per germ-carrier)

| micro-organism | Number of cycles | Formation time | Compound 1 | Compound 2 | Reduction of micro-organisms |
|---|---|---|---|---|---|
| S. aureus + 100 μl of sheep's blood | 3 | 900 s | $H_2O_2$ | — | 3.87 $\log_{10}$ |
| S. aureus + 100 μl of sheep's blood | 3 | 900 s | $H_2O_2$ | $CH_3COOH$ | 7.90 $\log_{10}$ |
| S. aureus + 100 μl of sheep's blood | 3 | 900 s | $H_2O_2$ | $CH_3COOH$ | <8.11 $\log_{10}$ |
| E. hirae + 100 μl of sheep's blood | 3 | 900 s | $H_2O_2$ | — | 2.23 $\log_{10}$ |
| E. hirae + 100 μl of sheep's blood | 4 | 600 s | $H_2O_2$ | $CH_3COOH$ | ≧7 $\log_{10}$ |
| E. hirae + 100 μl of sheep's blood | 3 | 900 s | $H_2O_2$ | $CH_3COOH$ | <7.8 $\log_{10}$ |
| E. coli + 100 μl of sheep's blood | 3 | 900 s | $H_2O_2$ | $CH_3COOH$ | <7.69 $\log_{10}$ |
| E. Coli + 100 μl of sheep's blood | 5 | 480 s | $H_2O_2$ | — | 1.38 $\log_{10}$ |
| E. coli + 100 μl of sheep's blood | 3 | 900 s | $H_2O_2$ | $CH_3COOH$ | ≧8 $\log_{10}$ |
| E. coli + 100 μl of sheep's blood | 3 | 900 s | $H_2O_2$ | $CH_3COOH$ | <8 $\log_{10}$ |
| P. aeruginosa + 100 μl of sheep's blood | 5 | 480 s | $H_2O_2$ | — | 1.47 $\log_{10}$ |
| P. aeruginosa + 100 μl of sheep's blood | 4 | 900 s | $H_2O_2$ | $CH_3COOH$ | 7 $\log_{10}$ |
| P. aeruginosa + 100 μl of sheep's blood | 3 | 900 s | $H_2O_2$ | $CH_3COOH$ | ≧8.25 $\log_{10}$ |
| P. aeruginosa + 100 μl of sheep's blood | 3 | 900 s | $H_2O_2$ | $CH_3COOH$ | 8.47 $\log_{10}$ |
| M. smegmatis + 100 μl of sheep's blood | 3 | 900 s | $H_2O_2$ | — | 2.47 $\log_{10}$ |
| M. smegmatis + 100 μl of sheep's blood | 4 | 600 s | $H_2O_2$ | $CH_3COOH$ | ≦7 $\log_{10}$ |
| M. smegmatis + 100 μl of sheep's blood | 3 | 900 s | $H_2O_2$ | $CH_3COOH$ | ≦7.6 $\log_{10}$ |
| M. smegmatis + 100 μl of sheep's blood | 3 | 900 s | $H_2O_2$ | $CH_3COOH$ | ≦8 $\log_{10}$ |
| C. albicans + 100 μl of sheep's blood | 3 | 900 s | $H_2O_2$ | — | 1.8 $\log_{10}$ |
| C. albicans + 100 μl of sheep's blood | 3 | 900 s | $H_2O_2$ | $CH_3COOH$ | ≧8.04 $\log_{10}$ |
| C. albicans + 100 μl of sheep's blood | 3 | 900 s | $H_2O_2$ | $CH_3COOH$ | ≧8.04 $\log_{10}$ |
| C. albicans + 100 μl of sheep's blood | 3 | 900 s | $H_2O_2$ | $CH_3COOH$ | <8 $\log_{10}$ |
| B. subtillis spores + 100 μl of sheep's blood | 3 | 480 s | $H_2O_2$ | — | 3 $\log_{10}$ |
| B. subtillis spores + 100 μl of sheep's | 5 | 600 s | $H_2O_2$ | $CH_3COOH$ | ≧3 $\log_{10}$ |

TABLE-continued

Number of viable and sporular bacterial forms destroyed in a sterilization chamber on a pad in the presence of blood of a sheep (100 $\mu$l per germ-carrier)

| micro-organism | Number of cycles | Formation time | Compound 1 | Compound 2 | Reduction of micro-organisms |
|---|---|---|---|---|---|
| blood | | | | | |
| B. subtillis spores + 100 $\mu$l of sheep's blood | 4 | 600 s | $H_2O_2$ | $CH_3COOH$ | $\geq 6 \log_{10}$ |
| B. subtillis spores + 100 $\mu$l of sheep's blood | 4 | 900 s | $H_2O_2$ | $CH_3COOH$ | $\geq 6 \log_{10}$ |
| B. subtillis spores + 100 $\mu$l of sheep's blood | 3 | 900 s | $H_2O_2$ | $CH_3COOH$ | $4 \log_{10}$ |
| B. stearoth spores + 100 $\mu$l of sheep's blood | 5 | 480 s | $H_2O_2$ | — | $<4 \log_{10}$ |
| B. stearoth spores + 100 $\mu$l of sheep's blood | 4 | 600 s | $H_2O_2$ | $CH_3COOH$ | $\geq 5 \log_{10}$ |
| B. stearoth spores + 100 $\mu$l of sheep's blood | 4 | 600 s | $H_2O_2$ | $CH_3COOH$ | $\geq 5 \log_{10}$ |
| B. stearoth spores + 100 $\mu$l of sheep's blood | 3 | 900 s | $H_2O_2$ | $CH_3COOH$ | $\geq 5 \log_{10}$ |

The table shows that the germicide potency of the method according to the invention is markedly improved in comparison with the method where only the germicide compound $H_2O_2$ is used in combination with $O_3$.

What is claimed is:

1. A method for disinfecting and sterilizing microbial contaminated or infectious materials, the steps comprising:
   (a) loading the material for disinfecting and sterilizing into a vacuum-proof sterilization chamber;
   (b) introducing liquid hydrogen peroxide into the sterilization chamber so as to penetrate the material;
   (c) introducing liquid acetic acid into the sterilization chamber so as to penetrate the material;
   (d) evacuating gas from the sterilization chamber so as to evaporate the liquid at least partially;
   (e) introducing gaseous ozone into the sterilization chamber; and
   (f) treating the material in a sterilization chamber for a sufficient time period so as to disinfect and sterilize the materials.

2. The method of claim 1 wherein the steps (b) and (c) are carried out in any sequence and wherein peracetic acid is generated in the sterilization chamber.

3. The method of claim 1 wherein the steps (b) and (c) are carried out simultaneously and wherein peracetic acid is generated in the sterilization chamber.

4. The method of claim 1 wherein the method is carried out at a temperature of about 15° C. to 35° C.

5. The method of claim 4 wherein the method is carried out at ambient temperature.

6. The method of claim 2 wherein the hydrogen peroxide and the acetic acid of steps (b) and (c) are introduced in two separate ampoules having such properties that after the evacuation of step (d) they burst with release of their content.

7. The method of claim 3 wherein the hydrogen peroxide and the acetic acid of steps (b) and (c) are introduced in a container having at least two compartments being constructed in such a manner that their contents are released is during the evacuation of step (d).

8. The method of claim 7 wherein the container has a compartment with a catalyst for shifting the equilibrium of the reaction equation

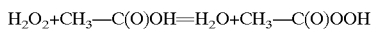

$$H_2O_2 + CH_3\!-\!C(O)OH = H_2O + CH_3\!-\!C(O)OOH$$

to the right, which catalyst is released at the same time as the hydrogen peroxide and the acetic acid.

9. The method of claim 8 wherein the catalyst is sulfuric acid.

10. The method of claim 1 wherein in step (f) the ozone and the formed peracetic acid are present in the vapor phase.

11. The method of claim 1 wherein the steps (b) to (e) are carried out at least two times.

12. The method of claim 1 wherein the sterilization chamber includes feeding means for feeding hydrogen peroxide, acetic acid and ozone into the chamber.

13. The method of claim 1 wherein the molar ratio of acetic acid to ozone is 3/1 to 1/3.

14. The method of claim 1 wherein the humidity in step (e) or (f) is at least 10%.

15. The method of claim 1 wherein the material is infectious waste in a solid or liquid state.

16. The method of claim 2 for treating contaminated or infectious waste wherein the waste is ground before, during or after step (b) or (c).

17. The method of claim 1 wherein step (e) is carried out at least twice.

* * * * *